United States Patent [19]

Sakane et al.

[11] 4,412,728
[45] Nov. 1, 1983

[54] FOCUSING APPARATUS FOR EYE-FUNDUS EXAMINING INSTRUMENT

[75] Inventors: Toshio Sakane; Haruhisa Madate; Yoshimi Kohayakawa, all of Yokohama, Japan

[73] Assignee: Canon Kabushiki Kaisha, Tokyo, Japan

[21] Appl. No.: 180,103

[22] Filed: Aug. 21, 1980

[30] Foreign Application Priority Data

Aug. 24, 1979 [JP] Japan .................. 54-107729

[51] Int. Cl.$^3$ .................. A61B 3/14; G03B 29/00
[52] U.S. Cl. .................. 351/206; 354/62
[58] Field of Search .................. 351/6, 7, 9, 14; 354/62

[56] References Cited

U.S. PATENT DOCUMENTS

| | | | |
|---|---|---|---|
| 3,016,000 | 1/1962 | Noyori | 351/206 |
| 3,614,214 | 10/1971 | Cornsweet et al. | 351/206 |
| 3,925,793 | 12/1975 | Matsumura et al. | 351/206 |
| 3,936,844 | 2/1976 | Matsumura | 351/7 |
| 4,149,787 | 4/1979 | Kobayashi | 351/7 |
| 4,187,014 | 2/1980 | Kato et al. | 351/7 |
| 4,208,107 | 6/1980 | Oharek | 351/7 |

Primary Examiner—John K. Corbin
Assistant Examiner—Rodney B. Bovernick
Attorney, Agent, or Firm—Fitzpatrick, Cella, Harper & Scinto

[57] ABSTRACT

An eye-fundus examining instrument is provided with a phototaking system, an illumination system for illuminating the fundus of an eye, a projecting system for projecting a focus mark and a comparison mark, a finder coupled to the phototaking system for observing therethrough the fundus of the eye, the focus mark and the comparison mark, a linear photosensor array for detecting the focus mark image reflected by the fundus of the eye, a light-receiving system focused to the fundus of the eye simultaneously with the phototaking system and the projecting system, a focusing mechanism for focusing the phototaking system to the fundus of the eye, a manual adjust member for manually driving the focusing mechanism, a servomotor for driving the focusing mechanism, a control circuit for controlling the servomotor by the output of the linear photosensor array, and a switch for selecting the power supply to the control circuit.

20 Claims, 19 Drawing Figures

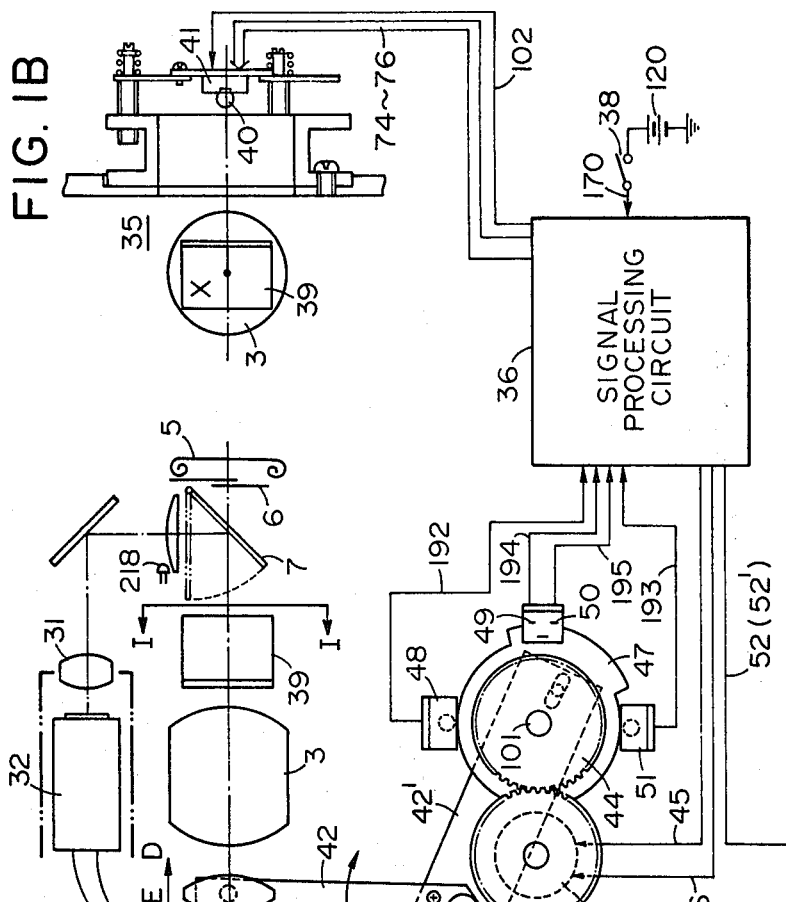
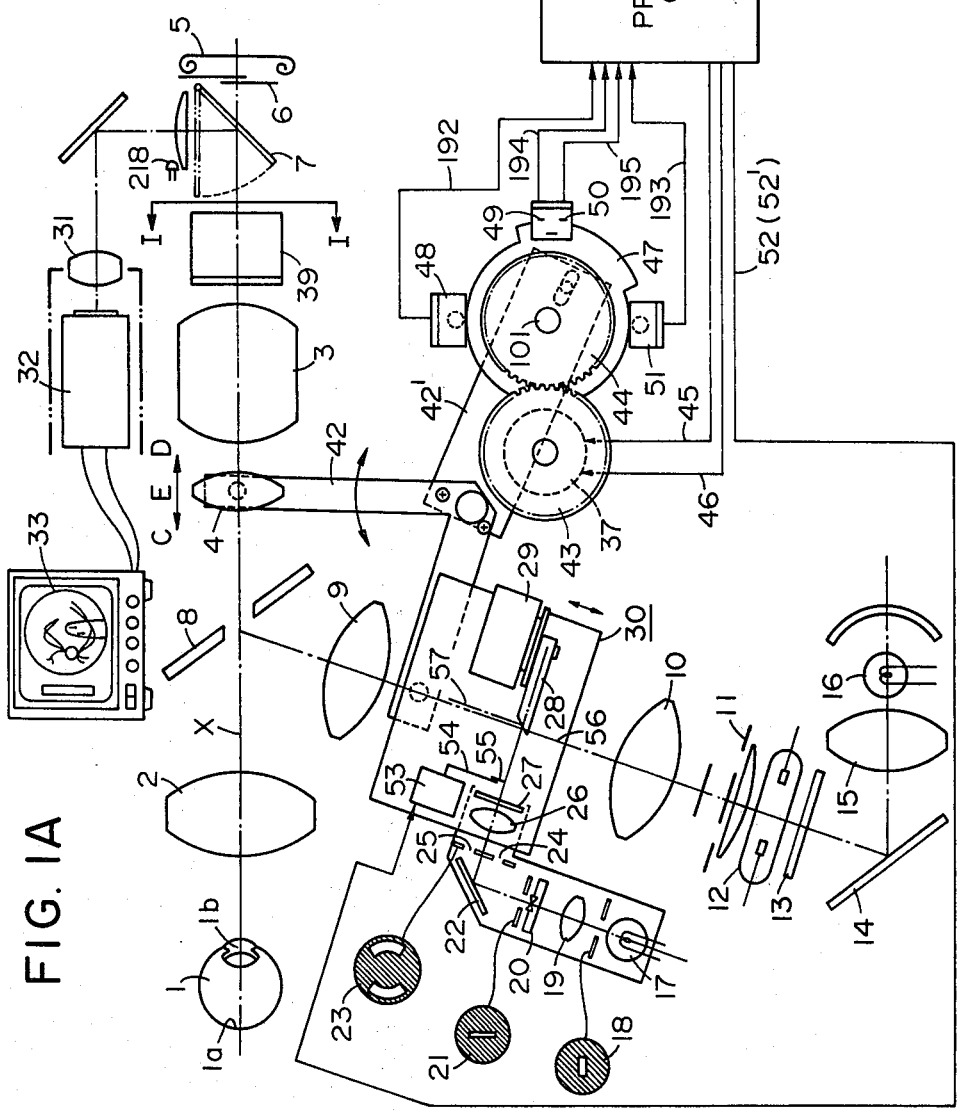

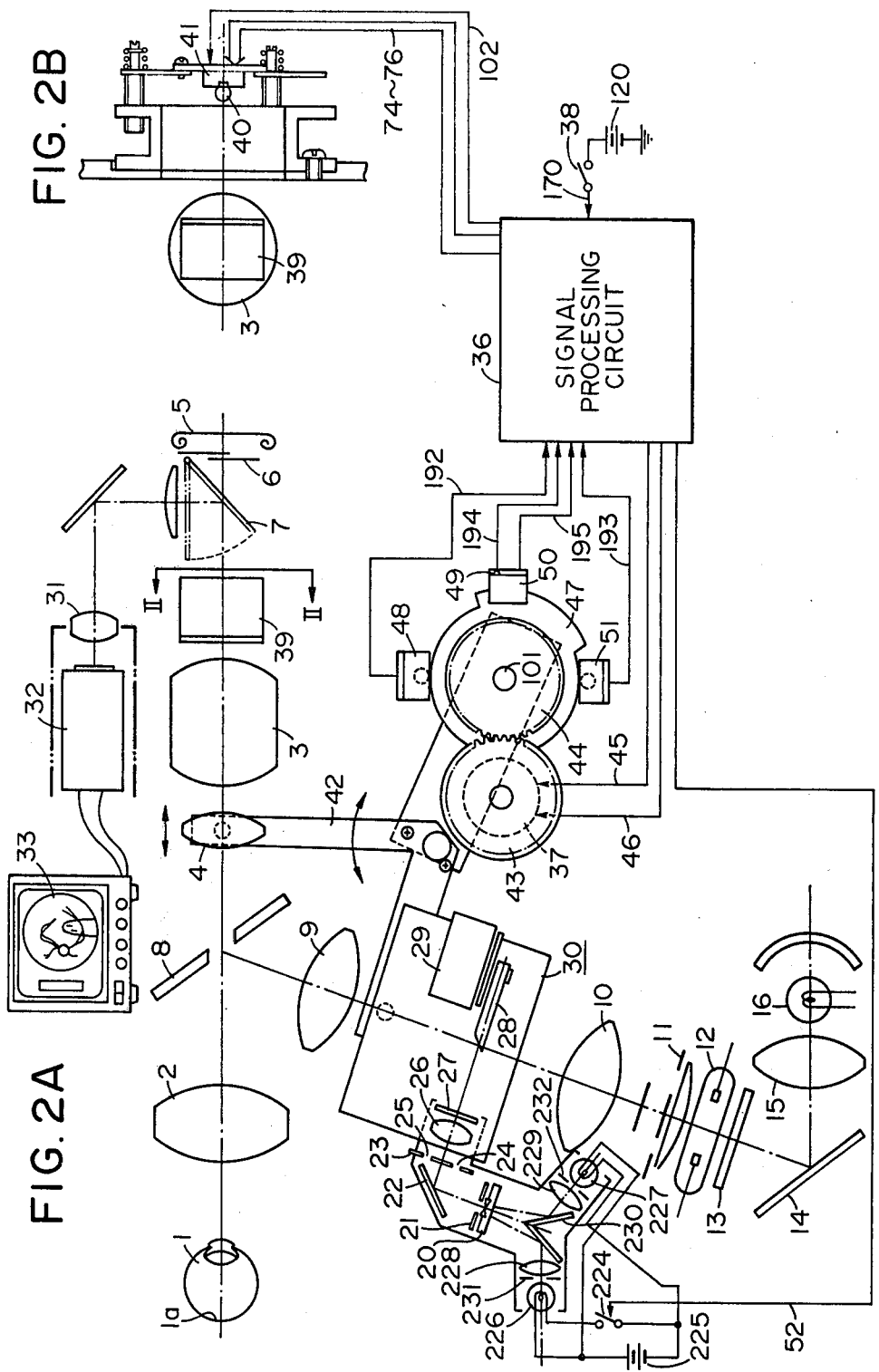

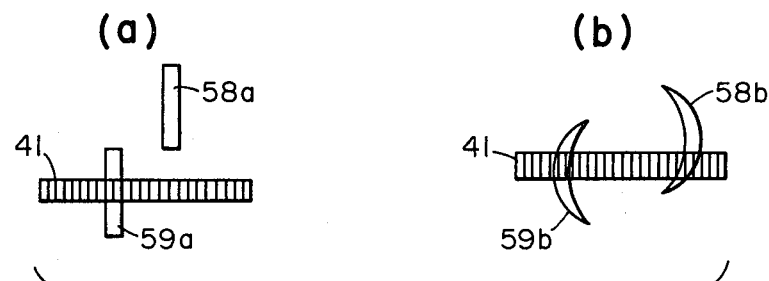
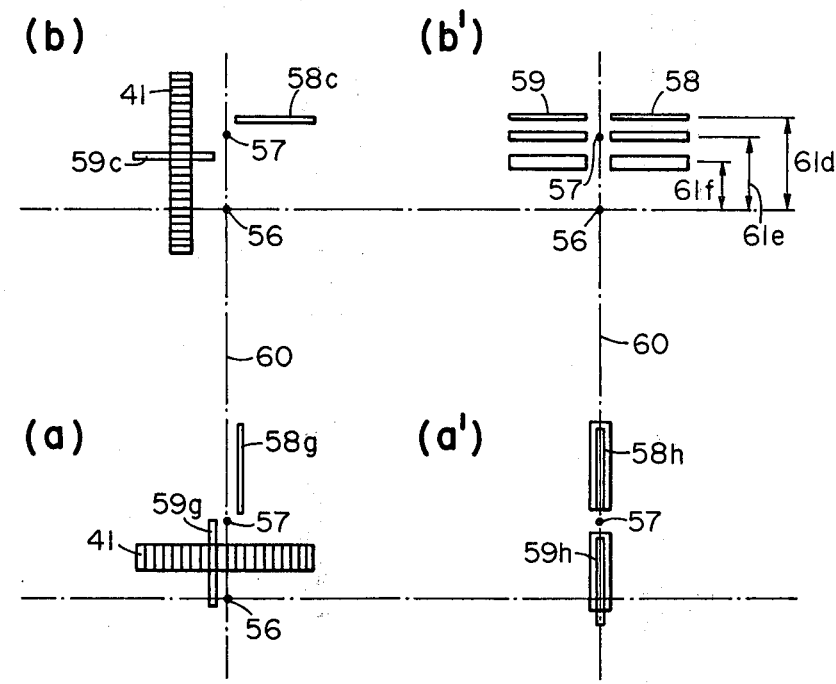
FIG. 3
FIG. 4

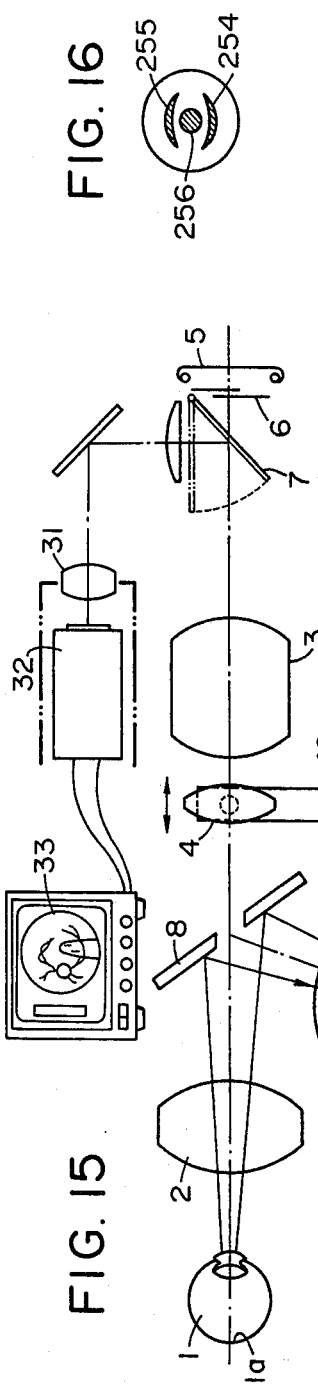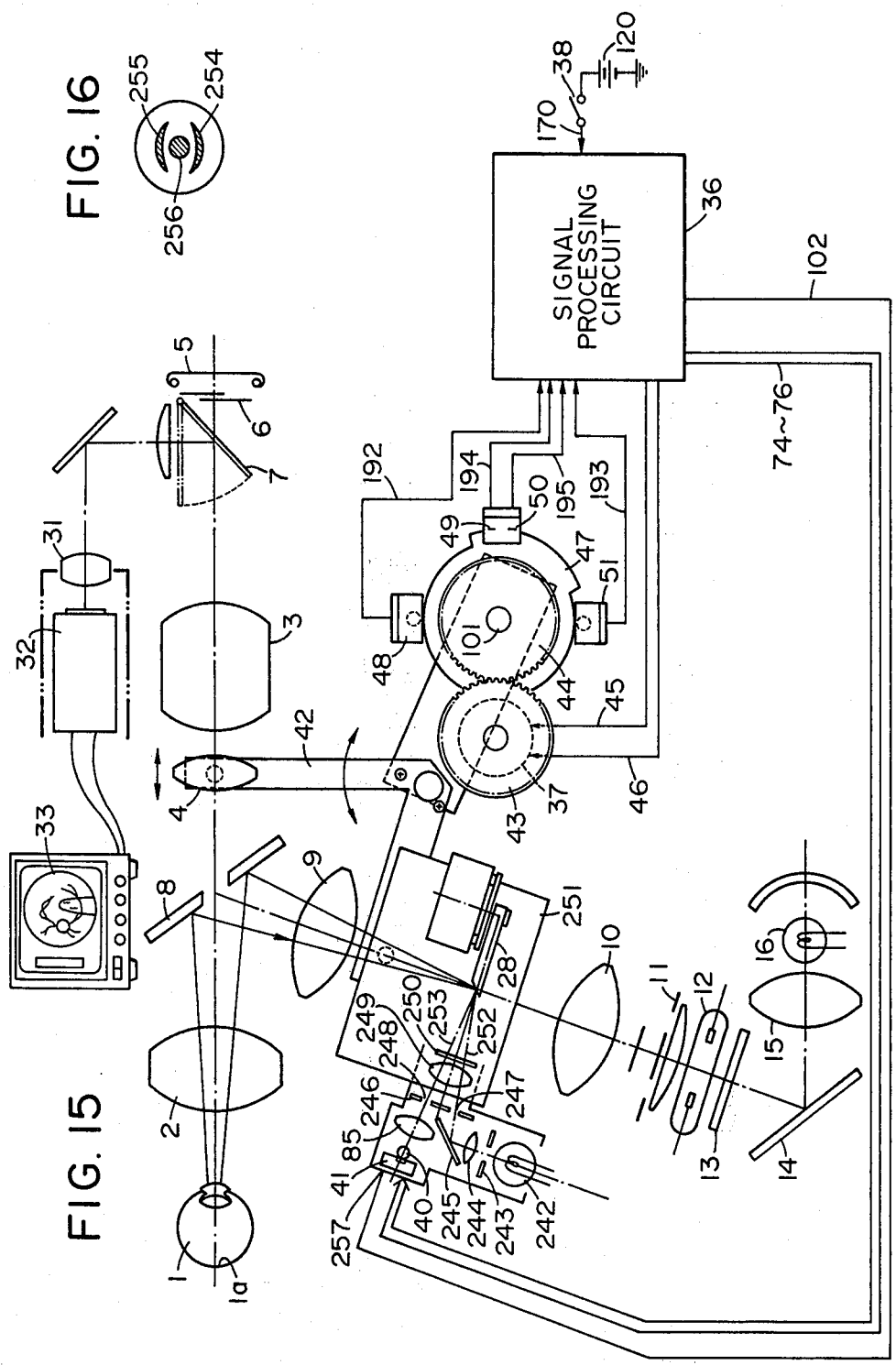

FOCUSING APPARATUS FOR EYE-FUNDUS EXAMINING INSTRUMENT

BACKGROUND OF THE INVENTION

1. Field of the Invention

The present invention relates to an eye examining instrument, and more particularly to a system for focusing the instrument to the fundus of the eye to be examined. The invention further relates to an improvement over U.S. patent application Ser. No. 109,275, now abandoned in favor of continuation U.S. patent application Ser. No. 346,870 by one of the inventors.

2. Description of the Prior Art

In a conventional eye-fundus camera, the focusing to the eye fundus has been achieved by adapting the sight of the eye to cross-hairs in the finder and by adjusting the photographing lens in such a manner that the eye fundus can be clearly viewed in this state. However, such focusing method inevitably involves personal fluctuation and is difficult to conduct rapidly.

U.S. Pat. No. 3,016,000 discloses a method of focusing the camera to the eye fundus by projecting a focus mark onto the eye fundus and adjusting the focusing lens so that the focus mark can be clearly viewed. Also, U.S. Pat. No. 3,925,793 (German Pat. No. 2,415,319) and U.S. patent application Ser. No. 945,845 disclose a focusing method by projecting plural marks on the eye fundus and aligning said marks under observation. Although a rapid focusing has been rendered possible by these methods, there still remains a strong demand for automatic focusing of the camera, as the setting of an eye-fundus camera simultaneously requires the alignment of the eye axis with the optical axis of the objective lens, the distance adjustment between the cornea and the objective lens and the focus adjustment. The operator has to constantly pay attention to these three factors as the above-mentioned alignment and distance are easily affected by small movements of the subject to be examined while the focusing is affected by a change in the sight of the eye to be examined. For this reason automatic focusing, if realized, will significantly alleviate the load on the operator and contribute to the probability of obtaining photographs of improved image quality. Also, in case of continuous photographing with successively displaced viewing fields, it becomes necessary to correct the focusing for each field displacement, and automatic focusing will contribute to the image quality in such case.

A pioneer invention for automatic focusing of the eye-fundus camera to the eye fundus is shown in U.S. Pat. No. 3,614,214, in which a dichroic mirror reflecting the infrared light but transmitting the visible light is provided in front of an ordinary eye-fundus camera in an oblique position to deflect the detecting beam from an automatic optometer toward the eye to be examined and to again deflect the reflected beam from the eye to said optometer, whereby the focusing lens of the eye-fundus camera is adjusted by the output of said optometer.

Now, even if the focusing to the eye fundus has come to be automatically executed, some time is required from the start of the detection until the adjustment is completed, and the examinee often moves and the refractive power of the eye fluctuates and therefore, the focus detecting apparatus always operates following the movement of the examinee and the variation in refractive power with a minute time delay. If the timing of the photographing release is bad, there will occur a disadvantage that photography is effected at a point of time whereat the focusing is still insufficient and thus, it is desirable that the completion of the focusing can be visually confirmed.

Also, where the crystalline lens of the examinee is turbid, it is often the case that the focus detecting apparatus does not sufficiently function and in such case, it is preferable that manual focus adjustment can be effected and further, since the retina is more or less thick, the necessity of manual focus adjustment occurs when it is desired to shift the focus of the camera to another position on the retina. In these cases, it is convenient to effect rough focusing to the eye fundus and then effect delicate focusing and for this purpose, a focus mark is caused to appear in the finder view field so that the degree of the focusing can be visually confirmed.

On the other hand, the aforementioned U.S. patent application Ser. No. 109,275, abandoned in favor of continuation U.S. patent application Ser. No. 346,870 has proposed a method whereby an index mark is projected upon the eye to be examined and the image thereof reflected by the eye fundus is directed onto two adjacent photoelectric conversion elements so that the focus adjusted condition can be known from the magnitude of the difference between the outputs of the two elements. In this method, where non-uniform background noise has ridden on the index mark, for example, where the brightness of the eye fundus around the index mark is non-uniform or where strong noise has ridden on the circumference of the index mark due to the reflection of the cornea, a great differential output and accordingly an error occurs in spite of the index mark lying at a predetermined position. Also, the light intensity of the index mark varies in accordance with movement of the eyeball and the differential output varies correspondingly, and this is inconvenient to the focus adjustment. Further, it has been empirically found that when the index mark is greatly deviated from the in-focus position, there is no difference between the two outputs and this is sometimes judged as in-focus by mistake.

SUMMARY OF THE INVENTION

It is a first object of the present invention to improve the focus detection accuracy and also prevent malfunctioning in an eye fundus examing instrument. To this end, in a specific embodiment which will hereinafter be described, a focus mark (bright line) is projected upon the eye fundus, the focus mark image reflected by the eye fundus is received by a photosensor array and the focus adjustment of a focus mark projecting system and a light-receiving system is effected so that the mark image lies at a reference position on the photosensor array.

It is a second object of the present invention to enable the focused condition of an eye fundus examining instrument to be visually confirmed. To this end, in a specific embodiment which will hereinafter be described, a focus mark and a comparison mark are caused to appear in the finder view field and when the examining instrument has been focused to the eye fundus, the focus mark and the comparison mark become juxtaposed.

It is a third object of the present invention to enable the examining instrument to be selectively focused manually and automatically.

It is a fourth object of the present invention to cause a comparison mark to become extinct as required in a construction wherein a comparison mark and a focus mark are moved at a time, because if the focus of the instrument is greatly changed, the comparison mark image reflected by the eye fundus will be distorted and enter onto a photosensor array to produce an incorrect signal.

It is a fifth object of the present invention to prevent the photosensor array from responding to a light beam forming the comparison mark in a construction wherein the comparison mark is stationary.

It is a sixth object of the present invention to vary the gain of a signal processing circuit in a staircase-like fashion in accordance with the peak value in the prescanning of the photosensor array and the gain in the prescanning.

It is a seventh object of the present invention to vary the focusing speed of the instrument by the magnitude of the distance between the focus mark image and the reference position of the photosensor array. In a specific embodiment which will hereinafter be described, if the distance between the focus mark image and the reference position of the photosensor array is great, the instrument is focused at a high speed and, if said distance becomes less than a predetermined value, the instrument is focused at a low speed.

It is an eighth object of the present invention to stop the focusing operation and further give warning when the reflection from the eyelid occurs due to winking of the examinee or when the setting of the instrument is so bad as to cause the reflection by the cornea.

It is a ninth object of the present invention to stop the focusing operation and further give warning when the photosensor array cannot detect the focus mark even if the instrument is focused a plurality of times.

It is a tenth object of the present invention to stop the focusing operation by an initial signal of the photographing release and to effect photographing by the next signal.

It is an eleventh object of the present invention to return the instrument to a condition in which it is focused to the fundus of the normal eye of zero diopter, after photographing has been terminated.

The invention will become fully apparent from the following detailed description thereof taken in conjunction with the accompanying drawings.

BRIEF DESCRIPTION OF THE DRAWINGS

FIG. 1A is a longitudinal cross-sectional view of a first embodiment of the present invention.

FIG. 1B is a view taken along the plane I—I of FIG. 1A.

FIG. 2A is a longitudinal cross-sectional view of a second embodiment of the present invention.

FIG. 2B is a partial view taken along the plane II—II of FIG. 2A.

FIGS. 3(a) and (b) illustrate the relation between the linear photosensor array and bright lines.

FIGS. 4(a), (a'), (b) and (b') illustrate the relation between the direction of bright lines and the linear photosensor array.

FIG. 15 is a longitudinal cross-sectional view of a fourth embodiment.

FIG. 16 shows the shape of a light beam as it passes through the eye-hole of the eye to be examined.

DESCRIPTION OF THE PREFERRED EMBODIMENTS

Figure 5:
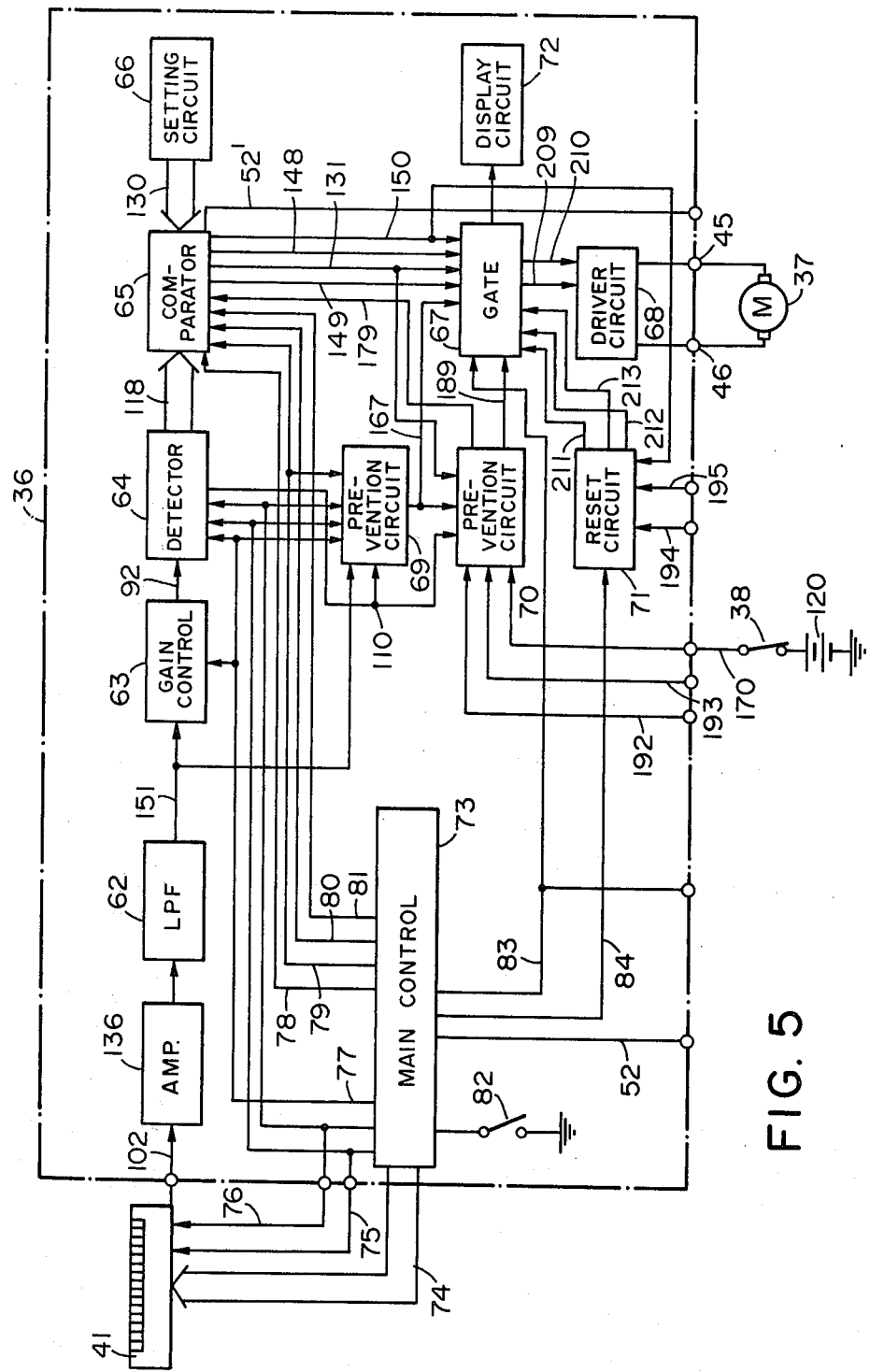
FIG. 5 is a block diagram of an electric circuit for processing the signal of the linear photosensor array of FIG. 1.

Referring to FIG. 1, reference numeral 1 designates an eye to be examined, 1a the eye-fundus, and 1b the pupil. Reference numeral 2 denotes an objective lens, 3 a phototaking lens, 4 a focus adjusting lens movable in the direction of the optical axis X, and 5 a photographing film. The objective lens 2 once forms the image of the eye-fundus 1a, and the focus adjusting lens 4 and phototaking lens 3 re-form this image on the film 5. Designated by 6 is a shutter adapted to be opened by a release mechanism, not shown. The members 2 to 6 together constitute a phototaking system. Denoted by 7 is a quick return mirror adapted to be retracted from the optical path by release of the shutter.

Designated by 8 is an apertured mirror obliquely disposed with respect to the optical axis. The opening thereof serves also as a phototaking diaphragm, but a diaphragm may be provided separately. This apertured mirror 8 is disposed conjugately with the pupil 1b with respect to the objective lens 2. Reference numerals 9 and 10 designate relay lenses, and reference numeral 11 denotes a ring slit provided with an annular opening. The ring slit 11 is provided conjugately with the pupil 1b with respect to the relay lenses 9, 10 and the objective lens 2. Reference numeral 12 designates a photographing strobo tube, 13 an infrared filter passing infrared light therethrough and intercepting visible light, 14 a mirror for bending the optical path, 15 a condenser lens, and 16 a white light source for observation. The light source 16 is conjugate with the ring slit 11 with respect to the condenser lens 15. The members 8 to 16 and the objective lens 2 together constitute an eye-fundus illuminating system.

The light from the light source 16 for observation passes through the condenser lens 15 and via the mirror 14 and through the infrared filter 13 to illuminate the ring slit 11. Further, the light having left the ring slit 11 passes through the relay lenses 10, 9 and is imaged on the mirror 8, where after it passes through the objective lens 2 and is re-imaged in the neighborhood of the pupil 1b an uniformly illuminates the eye-fundus 1a.

Reference numeral 17 designates a bright line projecting light source, 18 a field controlling slit, 19 a condenser lens, and 20 a split prism (bi-prism). The split prism 20 and the light source 17 are conjugate with respect to the condenser lens 19. Designated by 21 is a mask provided with a linear slit for supplying bright lines and disposed in proximity to the split prism. Denoted by 22 is a mirror for bending the optical path. Reference numeral 23 designates a two-aperture diaphragm which is substantially conjugate with the pupil 1b with respect to an interrupting optical system. The two-aperture diaphragm 23 is provided with openings 24 and 25 off the optical axis and intercepts on-axial rays. Each of the two light beams split and refracted by the split prism 20 passes through one of the openings 24 and 25. Designated by 26 is a projection lens. Denoted by 27 is an infrared filter having the same characteristic as that of the filter 13. The infrared filter 27 equalizes the wavelength ranges of the observation light beam and the bright line forming light beams. Designated by 28 is a mirror bar. The mirror bar 28 has an oblique mirror surface provided on one end thereof and the other end thereof is fixed to the rotary shaft of a rotary solenoid 29, so that when the solenoid 29 is operated upon photographing release, the mirror bar 28 is retracted out of the optical path. The members 17 to 29 together constitute a bright line projecting device 30. The projection lens 26 renders the mask 21 and the mirror surface of the mirror bar 28 conjugate and the device 30 is movable in the direction of the optical axis of the illuminating system and therefore, the movement of the device 30 brings the mask 21 and the eye-fundus 1a into conjugate relation.

On the other hand, reference numeral 42 denotes a trifurcated connecting arm rotatable about its support shaft. One of the three arms thereof is engaged with the focus adjusting lens 4 to transfer the lens 4 in the direction of the optical axis, and another arm thereof is engaged with the bright line projecting device 30 to transfer the device 30 in the direction of the optical axis. The remaining arm is pin-slot-coupled to a drive shaft 101 so that when the drive shaft 101 is reciprocally rotated, the arm 42' swings to move the focus adjusting lens 4 and the bright line projecting device 30 in the direction of the optical axis while satisfying a predetermined function. A focus dial, not shown, is mounted on the drive shaft 101 so as to enable the drive shaft 101 to be manually rotated in a simple manner.

The light source 16 for observation uniformly illuminates the eye-fundus while, on the other hand, the split bright line having left the projection unit 30 passes through the relay lens 9, the apertured mirror 8 and the objective lens 2 and is imaged in the shadow of the mirror bar on the eye-fundus 1a. The light reflected by the eye-fundus 1a passes through the objective lens 2, the aperture of the apertured mirror 8, the focus lens 4 and the phototaking lens 3 and is imaged on the film surface 5, but during observation, the light is projected via the quick return mirror 7 onto the image pick-up surface of an ITV camera 32 having a relay lens 31 and also having sensitivity to infrared range and is projected on a monitor TV 33. The relay lens 31, the ITV camera 32 and the monitor TV 33 together constitute an eye-fundus observation system. The image on the monitor TV 33 comprises the eye-fundus image having bright lines superposed thereon. Focus adjustment can be simply accomplished by manually rotating the drive shaft 101 while watching the monitor TV 33 so that the bright line image on the monitor TV 33 assumes a predetermined positional relation.

Now, in the present eye-fundus camera, provision is made of a bright line receiving device 35, a signal processing circuit 36, a motor 37, means for detecting the position of the focus adjusting lens, and manual/auto change-over means. The bright line receiving device 35 comprises a light splitting member 39, a cylindrical lens 40 (FIG. 1B) and a linear photosensor array 41, the light-receiving surface of which is coincident with the focal plane of the cylindrical lens 40. Also, the linear photosensor array 41 is disposed at a position conjugate with the imaginary fundus 1a of a normal eye with respect to a relaying optical system. The light splitting member 39 is disposed between the phototaking lens 3 and the quick return mirror 7 and may be, for example, a thin film mirror having the property of partly reflecting infrared light in an eye-fundus camera used for the observation by the use of infrared light and totally reflecting infrared light and totally passing visible light therethrough in an eye-fundus camera used for the observation by the use of visible light. The motor 37 is connected through gears 43 and 44 to the drive shaft 101 which causes the bright line projecting device 30 and the focus adjusting lens 4 to cooperate with each other, and accordingly, the motor 37 rotates the drive shaft 101 in response to the outputs 45, 46 of the signal processing circuit 36. The focus adjusting lens position detecting means comprises a sector 47 mounted on the drive shaft 101, and photocouplers 48, 49, 50, 51 disposed at predetermined positions on the outer periphery of the sector 47 and switched on and off by the sector 47, and applies a predetermined signal to the signal processing circuit 36 in accordance with the focus adjusting lens position. The manual/auto changeover means comprises a power source 120 and an electrical switch 38 and during automatic operation, as soon as the switch 38 is closed to activate the signal processing circuit 36, the change-over means puts out a signal 52 so that a bar 54 attached to a solenoid 53 or a light-intercepting plate 55 attached to the pointer 54 of a meter 53 is inserted into one of the two bright line optical paths of the bright line projecting system 30 which is not used for the detection of the bright line position, to thereby intercept such optical path. This intercepted optical path is the optical path of the bright line 58a in FIG. 3 which is projected through the opening 25. This light interception is such that, as shown in FIG. 3, in the bright line projecting device using the two-aperture diaphragm 23, when the camera is adjusted in the vicinity of the in-focus condition (FIG. 3(a), bright lines 58a and 59a are completely separated vertically in the drawing and do not overlap in the horizontal direction but, as the camera becomes deviated from the in-focus condition (FIG. 3(b), the bright line images approach the image of the two-aperture diaphragm 23 and thus, two bright line images occur on the linear photosensor array 41. To eliminate such phenomenon, during automatic operation, the bright line optical path which is not used for the detection of the bright line position is intercepted and only one bright line optical path is permitted to be projected.

However, as the camera approaches the in-focus condition, the two bright lines are separated vertically and therefore, when the focusing has been effected to such an extent that the bright line 58 separates from the linear photosensor array 41, the light-intercepting plate 55 may be retracted from the bright line optical path. On the other hand, during manual operation, the light-intercepting plate is stopped off the optical path and therefore, the two bright lines are projected so as not to harm the convenience of focus adjustment.

Part of the eye-fundus image reflected by the light splitting member 39 and the bright line light are bent in a direction perpendicular to the plane of the drawing sheet and pass through the cylindrical lens 40 and are imaged on the linear photosensor array 41. The scanning direction of the linear photosensor array is a direction perpendicular to the lengthwise direction of the bright lines, in other words, a direction becoming parallel to the optical axis of the phototaking system when it directs the light beam by one reflection, and the linear photosensor array is disposed so that the bright lines are coincident with each other at a particular position of the linear photosensor array. Also, the slit 18, prism 20, slit 21, two-aperture diaphragm 23 and quick return mirror bar 28 of the bright line projecting device 30 are disposed so that the lengthwise direction of the bright lines is parallel to an imaginary plane 60 formed by the optical axis 56 of the eye-fundus illuminating system and the optical axis 57 of the bright line projecting device in FIG. 4A, in other words, so that the split direction of the bright lines is perpendicular to the imaginary plane 60. Conversely, in an arrangement as shown in FIG. 4(b) wherein the lengthwise direction of the bright lines is perpendicular to the plane 60 and the bright lines are split parallel to the plane 60, the position whereat the two bright lines are coincident with each other changes as indicated by 61d, 61e and 61f in FIG. 4(b') in accordance with the visibility of the eye to be examined, and this is disadvantageous. In FIG. 4(a), the position whereat the bright lines are coincident does not depend on the visibility of the eye to be examined and lies on the plane 60, as shown in FIG. 4(a'). This step is one necessary only when the two optical axes 56 and 57 are deviated from each other, and is not necessary when these two optical axes are coincident with each other.

On the other hand, the signal processing circuit 36 is electrically coupled to the linear photosensor array 41 to receive the signal output of the linear photosensor array, detect the bright line position, drive the motor 37 in accordance with the bright line position and achieve the automatization of focus adjustment, and as shown in FIG. 5, it comprises an amplifier circuit 136, a low-pass filter (LPF) 62, a gain control circuit 63, a bright line position detecting circuit 64, a position comparator circuit 65, a reference position setting circuit 66, a gate circuit 67, a driver circuit 68, a malfunctioning prevention circuit 69, a non-stop (unlimited movement) prevention circuit 70, a reset circuit 71, a display circuit 72 and a main control circuit 73.

Figure 13:
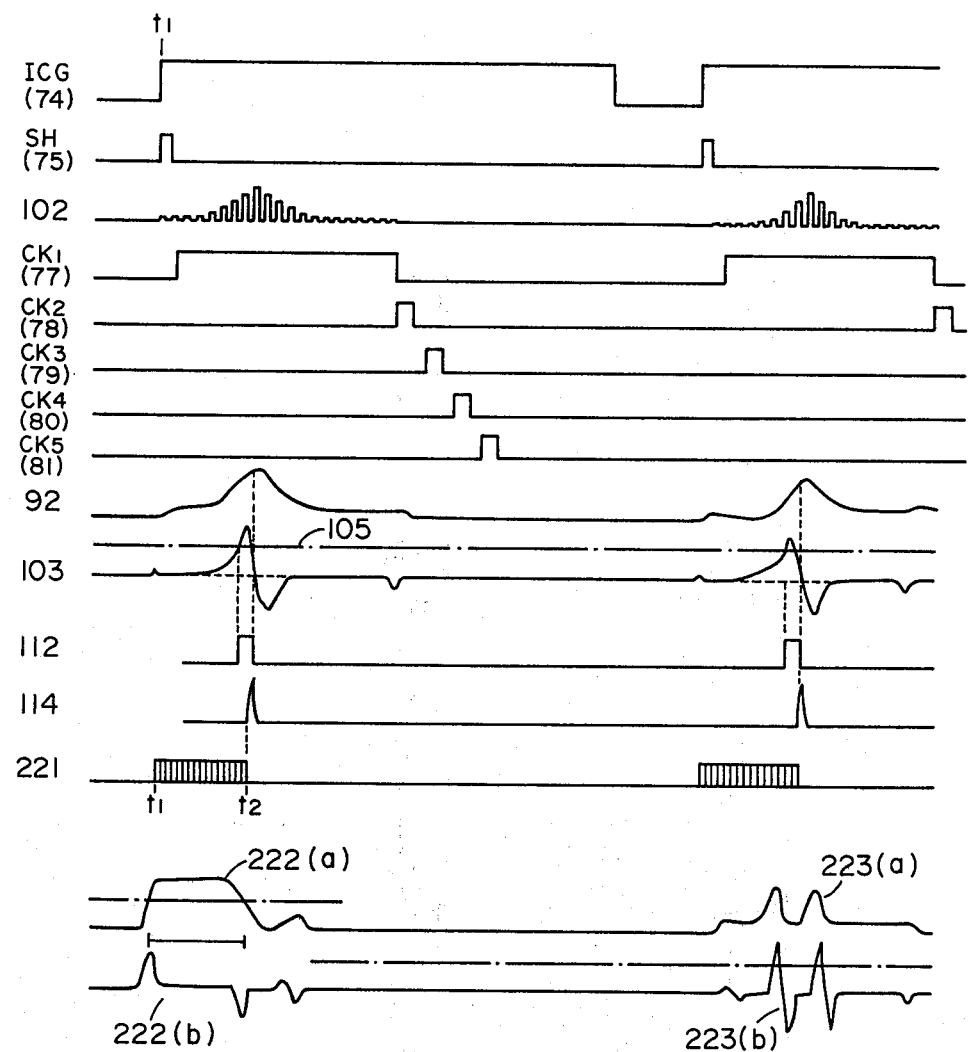
FIG. 13 shows signal waveforms related to the electric circuit of FIG. 5.

Each circuit will further be described in detail. The main control circuit 73 effects the control of each circuit portion of the signal processing circuit 36 and the control of the linear photosensor array 41. Some of control signals generated by the main control circuit 73 are shown in the time chart of FIG. 13. The linear photosensor array 41 receives a signal group 74 such as $\phi_1-\phi_4$, storage (IGG), OD and IS, and pulses such as transfer (SH) 75 and reset (RS) 76, and upon application of SH pulse 75 thereto, it puts out light information stored for a predetermined time, in accordance with the clocks $\phi_1-\phi_4$ (herein, a four-phase transfer PSCD is used as the linear sensor array). RS pulse 76 effects the reset for each 1 bit of the photocell. Also, (CK$_1$) 77 generates a pulse from the read-out starting time point or a time point delayed by a predetermined time from said time point until the read-out termination time point, and CK$_2$(78)-CK$_5$(81) generate a pulse on line 83 of a predetermined time in synchronism with the closing of a shutter switch 82 and a pulse on line 84 of a predetermined time in synchronism with the termination of the pulse on line 83. They also generate a light-intercepting or switch control signal on line 52 upon closing of a switch 38. The amplifier circuit 136 is an ordinary operational amplifier, and LPF 62 is a butterworth LPF.

Figure 6:
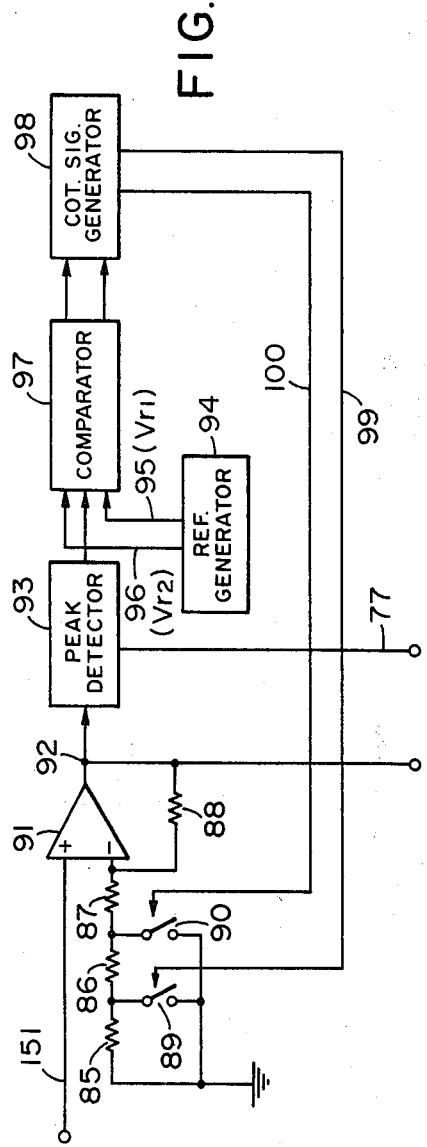
FIG. 6 is a diagram of a gain control circuit.

The gain control circuit 63 adopts the construction as shown in FIG. 6. Resistors 85–87 are series-connected between the negative (−) input terminal of an operational amplifier 91 and the ground, and the junctions between the resistors 85 and 86 and between the resistors 86 and 87, of a positive amplifier circuit negatively fed back by a resistor 88, are grounded through electrically controlled switches 89 and 90, and the gain is varied by closing-opening of these switches. The switches 89 and 90 detect the peak value of the output 92 of the amplifier 91 between the pulses (CK$_1$)77 by a detector circuit 93, and such peak value is compared, by a voltage comparator circuit 97, with a first reference value V$_{r1}$ 95 and a second reference value V$_{r2}$ 96 generated by a reference value generating circuit 94, and in response to the result of the comparison, a control signal generating circuit 98 generates signals on lines 99 and 100 which control the switches 89 and 90. The voltage comparator circuit 97 is a wind comparator and the control signal generating circuit 98 may comprise, for example, an up/down counter. When the switch 89 is closed and the peak value is lower than the reference value V$_{r1}$, the signal on line 100 becomes High and the signal on line 99 becomes Low and the switch 90 is closed while the switch 89 is opened, thus increasing the circuit gain. Further, in such condition, when the peak value is likewise lower than the reference value V$_{r1}$, the states of the control signals on lines 99 and 100 remain invariable because the gain is at an upper limit gain. Control signals 99 and 100 generally corresponding to the history of the gain can be generated in the control signal generating circuit 98 and the gain can be varied in a staircase-like fashion in accordance with the gain and peak value in the pre-scanning. By increasing the number of resistors and switches, it is possible to effect multi-stage gain control.

Figure 7:
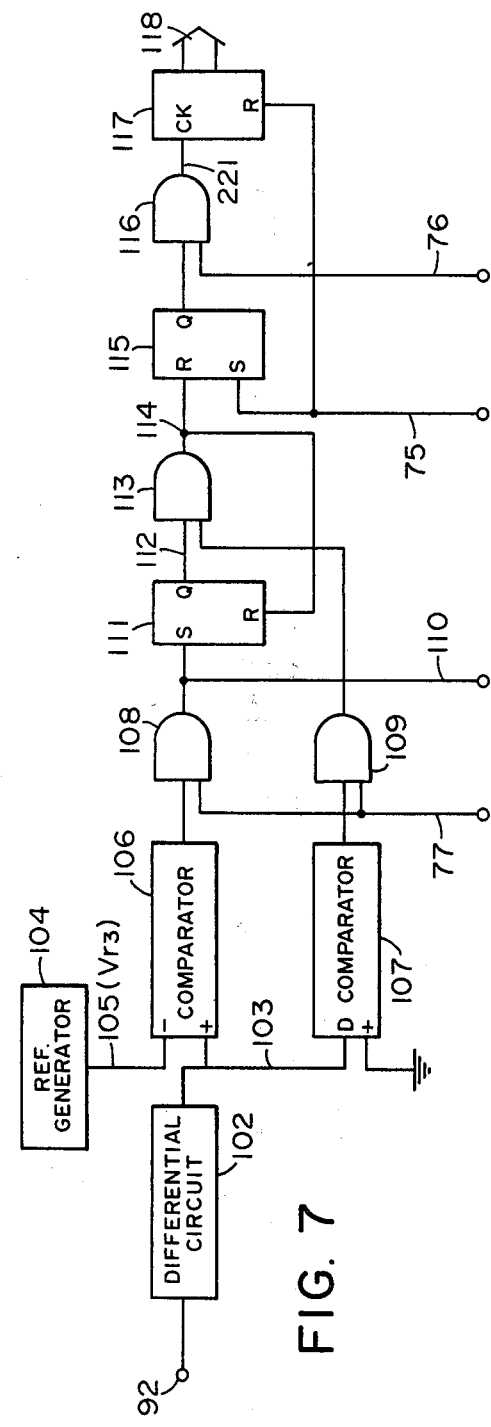
FIG. 7 is a diagram of a bright line position detecting circuit.

The bright line position detecting circuit 64 shown in FIG. 7 will now be described in detail. The output 92 of the gain control circuit 63 is differentiated by a predetermined time constant in a differential circuit 102, and the result 102' of the differentiation is compared, by a comparator circuit 106, with a reference value V$_{r3}$105 generated by a reference value generating circuit 104 and, when the result 103 is greater than the reference value V$_{r3}$105, the comparator circuit 106 puts out a High output. This output sets an R-S flip-flop (F/F) 111 through an AND gate 108 and renders Q output 112 thereof High. On the other hand, the differentiation result 103 is compared with zero value by a comparator 107, which puts out a High output when the differentiation result 103 is negative. The AND of this output and the Q output 112 is taken at an AND gate 113 through an AND gate 109, as a result of which it becomes 114. The High signal 114 resets R-S F/F 115. The AND of pulse RS 76 and the Q output of R-S F/F 115 is taken at an AND gate 116, and the pulse number during the time that the Q output of R-S F/F 115 is High is counted by a counter 117. The operation of the position detecting circuit 64 will be described with reference to the timing chart of FIG. 13. Gain-controlled signal 92 is differentiated and compared with the reference value V$_{r3}$105 and zero value. Of the High signals exceeding the reference value V$_{r3}$, only the High signal of period CK$_1$ is introduced into the gate 108 to set R-S F/F 113 and render Q output 112 High. The negative differentiated value period during the time that the Q output 112 is High is selected by an AND gate 113 to cause the output Q of R-S F/F 115 set by the read-out starting pulse SH 75 to be transited to low. The time point ($t_2$) of this transition to Low corresponds to the peak time point of a mountain-like signal. The counter 117 counts the pulse number of RS pulse 76 from the pulse 75 (time point $t_1$) until the transition time point ($t_2$) and puts out the result 118 of the count. Thus, the time from the read-out starting time point ($t_1$) to the peak position ($t_2$) of the first mountain of the signal whereat the differentiated value exceeds the reference value $V_{r3}$, namely, the position of the bright line on the linear sensor array, is measured by the counter 117.

Figure 8:
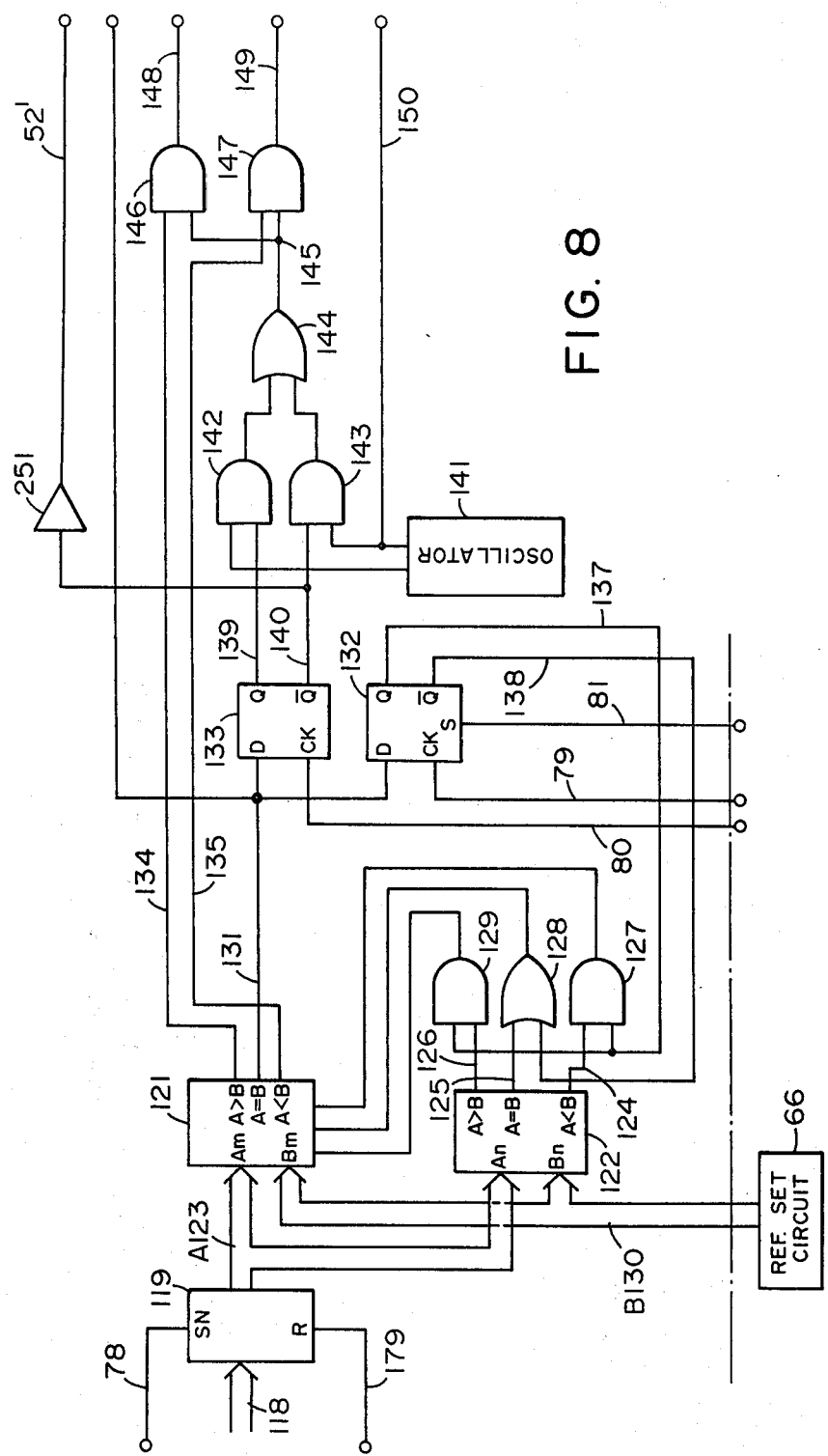
FIG. 8 is a diagram of a bright line position comparing circuit.

The bright line position comparator circuit 65 shown in FIG. 8 will now be described in detail. Designated by 119 is a (m+n) bit parallel input and parallel output shift register which transfers the count result 118 to comparators 121 and 122 at the first pulse $CK_2(78)$ after termination of the read-out. The shift register 119 causes its output 123 to be transited to Low when reset pulse 179 is High. The comparators 121 and 122 are comparators of m bits and n bits, respectively, and the comparison results 124, 125 and 126 of the least significant n bits are applied to the predetermined input terminals of the comparator 121 having the most significant m bits through an AND gate 127, an OR gate 128 and an AND gate 129 and as a whole, these comparators constitute a comparator of (m+n) bits, which compares a bright line position signal A123 with a reference position signal B130 set by the separately provided reference position setting circuit 66. The result 131 which is a A=B is applied to D of D-F/F 132 and D-F/F 133 and introduced at the timing of pulse $CK_3(79)$ and pulse $CK_4(80)$. Also, D-F/F 132 is set by pulse $CK_5(81)$ to render Q output 137 High and Q output 138 Low. Q output 137 is applied to AND gates 127 and 129 and Q output 138 is applied to OR gate 128. Now, when the read-out of the linear photosensor array 41 is terminated, bright line signal 118 is applied to A terminals of the comparators 121 and 122 at $CK_2(78)$ and compared with the reference position signal B130. Of the results of the comparison, the result 131 which is A=B is introduced at $CK_3(79)$ and when the result 131 is Low, that is, when A and B are not coincident, Q 137 becomes Low and Q 138 becomes High, and the comparison result of the least significant n bits through the gates 127-129 is not applied to the most significant bit comparator but comparison of the most significant m bits alone is effected and, of the results of such comparison, the result 131 which is Am=Bm is introduced into D-F/F 133 at $CK_4(80)$. If the result 131 is High (that is, the most significant m bits are coincident and only the least significant n bits are incoincident), Q output 139 becomes High and Q output 140 becomes Low, and of two different frequencies $f_1$ and $f_2$ ($f_1 < f_2$) obtained by an oscillator 141, the lower frequency $f_1$ is selected through gates 142-144. Conversely, when the result 131 is Low (that is, both the most significant bits and the least significant bits are incoincident), Q output 139 becomes Low and Q output 140 becomes High, and the high frequency $f_2$ is selected. This selected condition is continued until $CK_4$ of the next scanning cycle. Next, D-F/F 132 is set at $CK_5(81)$, and the comparison result of the least significant bits is applied to the most significant bits and thus, comparison of all the original bits is effected. If the result is A>B at this time, signal 134 becomes High and the pulse train of one of $f_1$ and $f_2$ is put out on line 148 through an AND gate 146. As this time, the other comparison results 131 and 132 are Low. Also, if the result is A<B, signal on line 135 becomes High and the pulse train of one of $f_1$ and $f_2$ is put out on line 149 through an AND gate 147. Further, if the result is A=B, signals on liner 134 and 135 become Low and outputs on liner 148 and 149 become Low. By this circuit, the motor 37 is driven at low speed if the difference between the bright line position and the reference position is below a reference value, and driven at high speed if said difference is above the reference value, and the motor 37 will be stopped if said difference becomes zero. Further, the Q output 140 of D-F/F 133 is put out as signal 52' through a buffer 251 and moves a light-intercepting plate 55 through a rotary solenoid 53. That is, when the difference between the bright line position and the reference position is above the reference value (both the most significant bits and the least significant bits are not coincident), the signal 52' is High and one of the bright line projecting optical paths is intercepted, and when said difference is below the reference value (only the least significant bits are not coincident or in-focus condition exists), the signal 52' is Low and the light-intercepting plate is retracted out of the bright line projecting optical path to permit two bright lines to be projected upon the eye-fundus. This reference value corresponds to the degree to which the two bright lines are separated from each other to such an extent that the bright line not used for the position detection does not influence the linear photosensor array.

Figure 9:
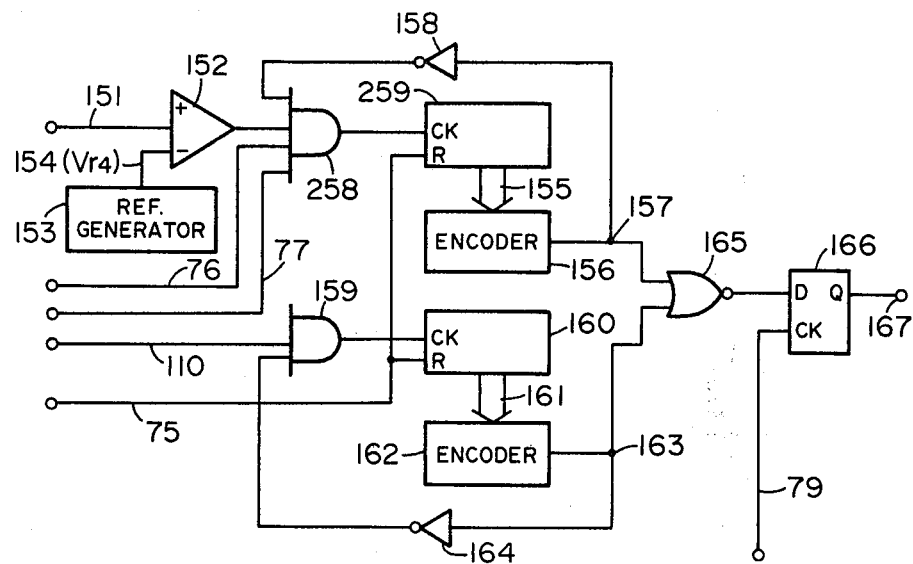
FIG. 9 is a diagram of a malfunctioning prevention circuit.

The malfunctioning prevention circuit 69 shown in FIG. 9 will now be described in detail. This circuit is intended to detect any noise which is considered to come into the eye-fundus camera and, when noise has come into the camera, to stop the motor 37 until the noise at least temporarily disappears. Here, two types of noise are taken into account. A first case is the case of uniform strong noise (shown at 222(a) in FIG. 13) which is experienced when the reflection by the eyelid resulting from winking has occurred. A comparator 152 compares the output 151 of LPF62 with a reference value $V_{r4}$ 154 generated by the reference value generating circuit 153, and puts out a High output if the output 151 is greater than the reference value $V_{r4}$. The AND of the High output and RS pulse on line 76 and pulse $CK_1(77)$ is taken at an AND gate 258, and the image element number (corresponding to RS pulse number of the linear photosensor array 41 for which the signal on line 151 during the read-out period $CK_1$ exceeds the reference value $V_{r4}$ is counted by a counter 259. If the count value 155 reaches a value preset in an encoder 156 comprising gates, output 157 is rendered High and enters an AND gate 258 through the inverter 158 to stop the subsequent counting. That is, when noise exceeding the reference value $V_{r4}$ and having a width greater than the set value has come into the camera during the read-out period $CK_1$, signal 157 is rendered High. Such condition is reset by a read-out starting pulse SH on line 75 in the next scanning. Now, a second counter-measure against noise is to cope with a case where the reflection by cornea has come into the camera (that is, to cope with the signal such as 223(a) in FIG. 13). The output 110 of the gate 108 of FIG. 7 is applied through an AND gate 159 to a counter 160, which counts the number of mountain-like signals of which the differentiated value during the read-out period $CK_1$ exceeds the reference value $V_{r3}$ (105). When the count value 161 exceeds the set value set by an encoder 162 comprising gates, output 163 is rendered High and applied to the AND gate 159 through an inverter 164 to stop the subsequent counting and the High state is maintained until the starting of the next read-out. The NOR of signals 157 and 163 is taken at a NOR gate 165 and the result is introduced into D-F/F 166 at time CK$_3$(79) and put out at 167. Only when both of the signals 157 and 153 are Low (that is, the set noise has come in), the output 167 becomes High to drive the motor 37 through the gate circuit 67 and driver circuit 68.

The non-stop preventing circuit 70 shown in FIG. 10 will now be described in detail. This circuit can stop the driving of the motor 37 when the bright line signal is so weak that the position signal 110 of the bright line position detecting circuit 64 is not put out even if the focus adjusting lens 4 is caused to effect one reciprocal movement, and also can prevent vibration of the focus adjusting lens 4 which will provide an eyesore, in order to effect display of a warning. The focus adjusting lens position detecting means, as previously described, comprises the sector 47 mounted on the drive shaft 101, and photocouplers 48-51 disposed at predetermined positions on the outer periphery of the sector 47, and the operation thereof will be described here with reference to FIG. 11. FIG. 11A shows the range of movement of the focus adjusting lens 4, E shows the zero diopter time (namely, the mid-point), and C and D show the ends of movement. FIG. 11B shows the sector portion, and the rotation of the sector through 180° causes the focus adjusting lens 4 to move over its range of movement. Designated by 47 is a sector provided on a disc 168 within a range of 90° thereof, and photocouplers 48–51 are installed at shown positions. At the zero diopter position, the sector 47 lies at a position indicated by solid line, and the photocouplers 49 and 50 put out conducted High outputs. Also, at one end C position, the sector 47 lies at a position indicated by dotted line, and the photo-coupler 48 is shielded from light and the output thereof becomes Low. At the other end D position, the sector 47 assumes a position indicated by dot-and-dash line and the output of the photo-coupler 51 becomes Low.

Figure 10:
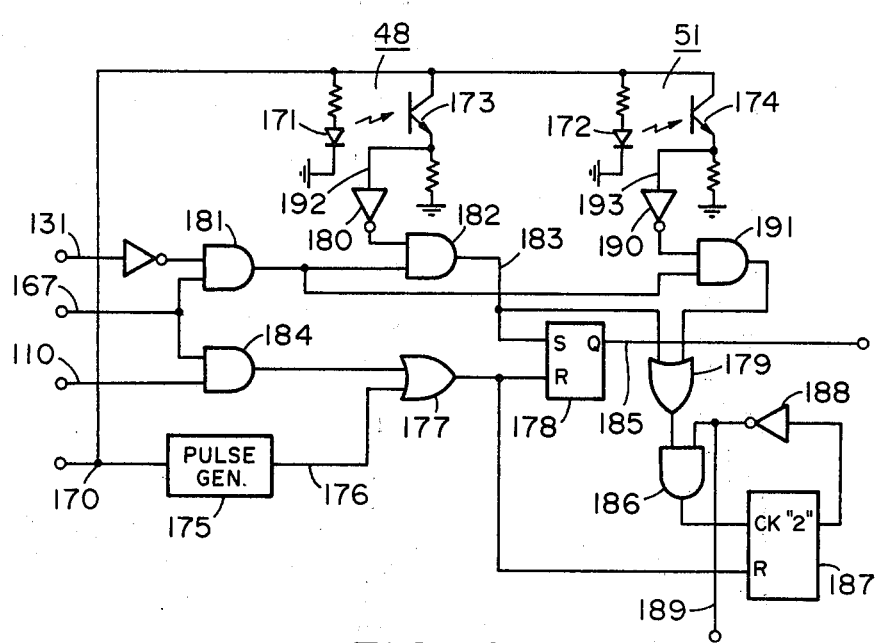
FIG. 10 is a diagram of a non-stop preventing circuit.
Figure 11A:
FIG. 11A diagrammatically shows the movement of a focus adjusting lens.
Figure 11B:
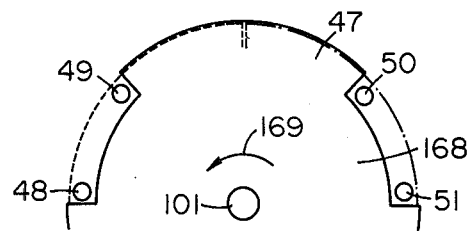
FIG. 11B illustrates the relation between a sector and a photocoupler.

In FIG. 10, it is to be understood that in a condition wherein a shift register 119 is not reset but normal comparison is effected, when there is no bright line position signal, the focus adjusting lens 4 of FIG. 1 is moved from D to E (from E to C) of FIG. 11 (sector rotation in the direction of arrow 169). Now, when the switch 38 is closed and the signal 170 of FIG. 10 becomes High, the photocouplers 48 and 51 are activated to turn on LEDs (light emitting diodes) 171 and 172 and are photocoupled to phototransistors 173 and 174. Simultaneously therewith, a pulse generating circuit 175 is triggered to generate a single pulse on line 176, which resets the counter 187 and R-SF/F 178 through an OR gate 177 to thereby render Q output 185 Low so as to permit normal comparison to be effected. If a position signal 110 remains Low and the focus adjusting lens 4 is driven to the position C, the space between the LED 171 and the phototransistor 173 is shielded from light by the sector 47 and the output of an inverter 180 becomes High. If, in this condition, the output 167 of the malfunctioning prevention circuit 69 is High (that is, there is no predetermined noise input) and incoincident (A=B output 131 is Low), High signal is applied to an AND gate 182 through an AND gate 181, so that the output 183 of the gate 182 becomes High to set R-SF/F 178 and render Q output 185 High, whereby abnormal comparison (the A inputs of the comparatos 121 and 122 of FIG. 8 are zero) is effected and the focus adjusting lens 4 is reversed (moved from C to E, D). Also, signal 183 enters the counter 187 through an OR gate 179 and an AND gate 186 and is counted by 1 count. The counter 187 is one having a decoded output. In this condition, when the position signal 110 in the case where no malfunctioning is taking place (output 167 is High) becomes High (the bright line position is detected), R-SF/F 178 is reset through an AND gate 184 and an OR gate 177, and Q output 185 is transited to Low, thus restoring normal comparison. Also, the High position signal 110 resets the counter 187 to cause it to be transited to the original zero count condition. Further, if the position signal 110 remains Low even during this abnormal comparison, the focus adjusting lens 4 will be moved to the D position of FIG. 11. If the lens 4 comes to this D position, LED 172 and phototransistor 174 are intercepted by the sector 47 and an inverter 190 assumes High level to cause an AND gate 191, an OR gate 179 and an AND gate 186 to progress the counting of the counter 187. When the count value becomes 2, the output 189 of an inverter 188 becomes Low and the subsequent counting is stopped through the AND gate 186, and this condition is maintained until the counter 187 is reset. The Low state of the signal 189 stops the driving of the motor 37 through the gate circuit 67 and the driver circuit 68 and also turns on and off a displayer 218 (FIG. 12) in the display circuit 72, thereby giving warning.

Figure 12:
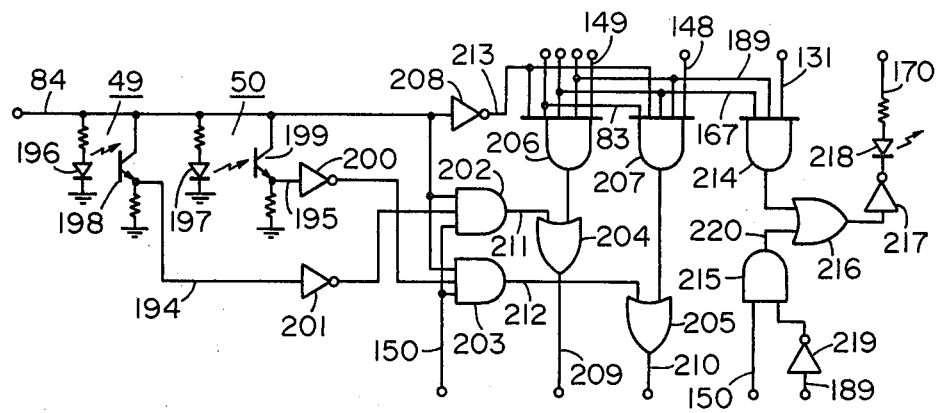
FIG. 12 is a diagram of a reset, gate and display circuit.

The reset circuit 71, the gate circuit 67 and the display circuit 72 will now be described with reference to FIG. 12, but before that, it is to be understood that the switch 82 shown in FIG. 5 is a switch for activating the X contact or shutter of the photographic camera and that the shutter is opened upon closing of this switch. Upon closing of the switch 82, the shutter is opened and the photographing is carried out and at the same time, a signal 83 (FIG. 12) which is Low during a predetermined time T$_1$ is put out from the main control circuit 73 to render the outputs of AND gates 206 and 207 Low during said time T$_1$, thus stopping the driving of the motor 37. A signal 84 which is generated in the main control circuit 73 in synchronism with the change of the signal 83 to High level or in synchronism with the closing of the shutter and which is High during a predetermined time T$_2$ activates the photocouplers 49 and 50. Simultaneously therewith, a signal which is inverted by an inverter 208 and which remains Low during the time T$_2$ is applied to AND gates 206 and 207 to render the outputs of the AND gates 206 and 207 Low during the time T$_2$. Now, the position of the focus ajdusting lens 4 during the period T$_2$ after termination of the photographing is detected by the photocouplers 49 and 50 and, for example, when the focus adjusting lens 4 lies at the C side from E of FIG. 11A, the LED 196 and phototransistor 198 constituting the photocoupler 49 are shielded from light by the sector 47 and the output 194 is in Low state. Such state is inverted to High state by an inverter 201, and a high frequency pulse train f$_2$(150) put out by the oscillator of FIG. 8 is applied to an OR gate 204 through an AND gate 202 to effect the movement of the focus adjusting lens 4 toward E, D from C of FIG. 11A. When the lens 4 comes to the E position, the outputs 194 and 195 of the photocouplers 49 and 50 become High to render the AND gate outputs 202 and 203 Low through inverters 201 and 200, whereby the lens 4 is inhibited from further moving. Conversely, when the focus adjusting lens 4 lies at the D side from E, the LED 197 and phototransistor 199 constituting the photocoupler 50 is shielded from light by the sector 47 and the output 195 becomes Low, and the motor 37 is driven through an inverter 200, an AND gate 203 and an OR gate 205, so that the focus adjusting lens 4 is moved from D toward E, C and stopped at the E position as described above. By applying T$_2$ signal 84 to the AND gates 202 and 203, signals during other than the period T$_2$ are neglected. By this reset circuit 71, the position of the focus adjusting lens of the eye-fundus camera returns to the vicinity of the zero diopter after termination of the photographing and thus, the camera can be ready for the next photographing in its best condition. In the gate circuit 67, a signal 209 passed through an AND gate 206 and an OR gate 204 effects the movement of the focus adjusting lens 4 from C toward E, D of FIG. 11A and a signal 210 passed through an AND gate 207 and an OR gate 205 effects the movement of the focus adjusting lens 4 from D toward E, C of FIG. 11A. Further, an AND gate 214 puts out a High output only the A=B signal 131 is High (in-focus) and signal 189 is High (the bright line position has been detected) and signal 167 is High (a predetermined noise has not been applied as input), to thereby turn on LED 218 through an OR gate 216 and an inverter 217, thus displaying the in-focus condition. Also, when signal 189 is Low (the driving of the focus adjusting lens 4 has been stopped by the non-stop preventing circuit 70), this signal 189 is inverted by an inverter 219 and a pulse train 150 is put out 220 through an AND gate 215, and this pulse train 220 turns on and off LED 218 through the OR gate 216 and the inverter 217, thus effecting the display of a warning. Next, the driver circuit 68 amplifies the outputs 209, 210 of the gate circuit 67 to provide outputs 45, 46 and it comprises a transistor or the like.

The circuits 61-73 included in the signal processing circuit 36 shown in FIG. 5 have thus far been described in detail, and the operations thereof will hereinafter be described. When the switch 38 is closed, the signal processing circuit 36 is activated and the motor 37 is rotated by signals 45 and 46, so that the drive shaft 101 connected through gears 43 and 44 is rotated to cause the main arm 42' of the connecting arm 42 to swing, whereby the bright line projecting system 39 engaged with the bifurcated arm and the focus adjusting lens 4 start to move. On the other hand, with this switch 38 closed, the light-intercepting member 55 adapted to be driven in response to signal 52 is inserted in the optical path of one of a pair of bright lines and the infrared bright line (58 in FIG. 3) which is not used for the bright line detection is not projected upon the eye-fundus 1a or not projected until focusing is effected to some extend. The reflected image of the infrared bright line (59 in FIG. 3) projected upon the eye-fundus is formed on the linear sensor array through the light splitting member 39 and the cylinder lens 40. The signal output 102 of the linear sensor array 41 is passed through an amplifier circuit 136 and LPF 62 an amplified in the gain control circuit 63, whereafter the bright line position detecting circuit 64 detects the position of the projected infrared bright line on the linear sensor array 41, and the position comparator circuit 65 compares the bright line position with the reference position 130 set by the reference position setting circuit 66 and drives the motor 37 through the gate circuit 67 and the driver circuit 68 so that the difference between said two positions becomes zero, whereby effecting automatic adjustment of the movement of the focus adjusting lens 4. When, during this focus adjustment, any bright line signal other than the predetermined one (the so-called predetermined noise signal) has been superposed upon signal 102, the driving of the motor 37 is stopped by the malfunctioning prevention circuit 69 through the gate circuit 67 and the driver circuit 68 until said predetermined noise signal is eliminated. Also, where, during the focus adjustment, the predetermined bright line signal is not applied as input, the driving of the motor 37 is stopped by the non-stop preventing circuit 70 through the gate circuit 67 and the driver circuit 68 until a bright line position signal 110 is put out, and at the same time, the display circuit 72 is turned on and off to effect display. When the focus becomes coincident by the above-described operation, the motor is stopped through the gate circuit 67 and the driver circuit 68 and at the same time, the display circuit 72 is turned on to effect display. In this in-focus condition, when the switch 82 is closed (the shutter 6 is opened), the quick return mirror 7 is retracted from the phototaking optical path and the photographing strobo 12 is turned on to effect photography, but during this period, the motor 37 is stopped through the gate circuit 67 and the driver circuit 68 without depending on the content of the signal 102. Now, when the shutter 6 is closed and the photography is terminated, the motor 37 is driven by the reset circuit 71 and the focus adjusting lens position detecting means through the gate circuit 67 and the driver circuit 68 to return the bright line projecting system 30 and the focus adjusting lens 4 to the vicinity of zero diopter, thus becoming ready for the next photography. When the switch 38 is not closed, the same operation as that of the conventional manually operated eye-fundus camera is effected, that is, the drive shaft 101 is manually rotated to effect the focus adjustment. Also, in this case, the pair of bright lines are projected upon the eye-fundus.

Now, FIG. 2 shows a different second embodiment. The portion of the second embodiment which differs from the first embodiment is the construction of the bright line projecting system 30. The bright line projecting system 30 in the second embodiment has two different light sources 226 and 227 for projecting a pair of bright lines, respectively, and the lights from these light sources respectively pass through slits 231 and 232 and lenses 228 and 229 and are reflected by a mirror 230, and pass through a split prism 20, a slit 21 and via a mirror 22 to irradiate the slits 25 and 24 of a two-aperture slit 23, and further pass through a lens 26 and an infrared filter 27 and are imaged on a quick return mirror 28. After being reflected by the quick return mirror 28, the lights are projected upon the eye-fundus 1a as previously described. Now, the two light sources are turned on by a power source 225 and the light source 226 for projecting the bright line which is not used for the position detection is turned off during automatic operation by a switch 224 adapted to be opened by the High signal of signal 52, and only the bright line which is used for the position detection (59 in FIG. 3) is projected. The other operations are similar to those of the previously described first embodiment.

Figure 14:
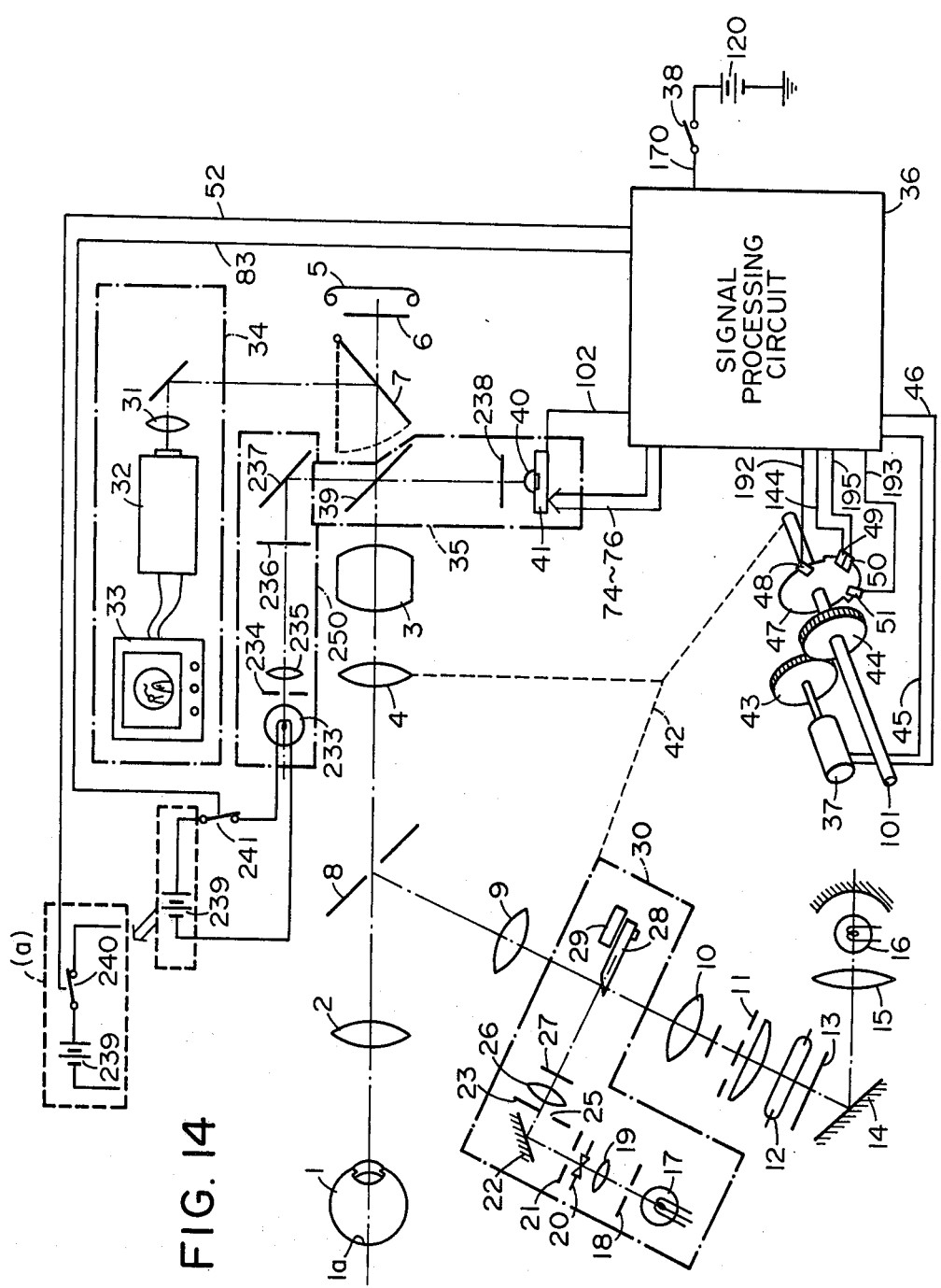
FIG. 14 is a longitudinal cross-sectional view of a third embodiment.

FIG. 14 shows a third embodiment. The third embodiment differs from the first embodiment in that only a slit 25 is provided in the two-aperture slit 23 of the bright line projecting system 30, that is, only a first bright line used for the position detection (59 in FIG. 3)

is projected upon the eye-fundus 1a, that light-intercepting portions 53, 54 and 55 are eliminated and that the bright line receiving system is arranged as shown and a filter 238 is inserted between the light splitting member 39 and the linear photosensor array 41.

Further, a second bright line projecting system 250 different from the bright line projecting system 30 is newly provided so that by the second bright line projecting system 250, a second bright line is projected through the light splitting member 39 onto a particular position on the image pick-up screen of the ITV camera 32 of the eye-fundus observation system 34 so as to form a pair with the first bright line on the image pick-up screen and when the two bright lines assume a particular positional relation, in-focus condition takes place. The first bright line is displaced with the movement of the focus adjusting lens, while the second bright line is fixed. The second bright line projecting system 250 comprises a light source 233, a slit 234 on the optical axis, a lens 235, a filter 236 and a mirror 237, and now, where the filter 236 is an infrared cassette filter (that is, the second bright line is visible light), a filter 238 is made into a visible light cutting and infrared light transmitting filter so that the second bright line is not projected upon the linear photosensor array. In this case, the light source 233 is turned on by a power source 239 through the switch 241, but during photography, the switch 241 is opened by signal 83 and the light source 233 is turned off, so that the second bright line is not projected. Also, where the filter 236 is made into a visible light cutting and infrared light transmitting filter (that is, the second bright line, too, is infrared light), the filter 238 is not installed and the dotted parentheses of FIG. 14 are replaced by the circuit shown at (a) in FIG. 14 and the light source 233 is turned on by the power source 239 through switches 240 and 241, and during automatic operation, the switch 240 is opened by signal 52 and during photography, the switch 241 is opened by signal 83 and the light source 233 is turned off, so that the second bright line is not projected. The other operations are similar to those of the first embodiment.

FIG. 15 shows a fourth embodiment. In this embodiment, the bright line projecting system 251 comprises a light source 242, a slit 243, a lens 244, a mirror 245, a ring slit 246, a lens 249, an infrared transmitting filter 250 and a quick return mirror 28. The slit 243 is disposed on a plane conjugate with the eye-fundus 1a, and the ring slit 246 is disposed at a position conjugate with the iris of the eyeball. The light from the light source 242 irradiates one aperture 247 of the ring slit 246 through the slit 243, the lens 244 and the mirror 245. The light leaving the aperture 247 passes through one half surface of the lens 249, whereafter it is projected upon the eye-fundus 1a through the filter 250, the quick return mirror 28, the relay lens 9, the apertured mirror 8, the eyepiece 2 and part of the pupil (the image 254 on the pupil plane of the ring slit aperture 247 shown in FIG. 16). The bright line is displaced by the movement of the eye-fundus illuminating system of the bright line projecting system in the direction of the optical axis and during the focusing, it is projected always onto a particular position. Now, the eye-fundus reflected image of the projected bright line is taken out from the central portion 256 of the pupil and other portions of the pupil (the image 254 shown in FIG. 16 and the image 255 on the pupil plane of the ring slit aperture 248 symmetrical with respect to the optical axis), and the bright line image taken out from the central portion is projected upon the photographing surface of the ITV camera 32 through the objective lens 2, the aperture of the apertured mirror 8, the focus adjusting lens 4, the phototaking lens 3, the quick return mirror 7 and the relay lens 31, as previously described, and is observed with the eye-fundus image in the monitor TV 33. On the other hand, the bright line image taken out from the other portion of the pupil passes through the objective lens 2, the apertured mirror 8, the quick return mirror 28, the filter 250 and the other half surface of the lens 249 and passes through the aperture 248 of the ring slit 246 to a light-receiving system 257 disposed rearwardly of the two-aperture slit 246 on the optical path 253, that is, passes through the lens 85 and the cylindrical lens 40 and is imaged on the linear photosensor array 41. The linear sensor array 41 is disposed in a plane conjugate with the eye-fundus 1a on the optical path 253 and is scanned in a direction perpendicular to the lengthwise direction of the bright line. The light-receiving system 257 is moved with and similarly to the bright line projecting system 251. Thus, in the same manner as already described, the bright line position is detected and the bright line projecting system 251 and the focus adjusting lens 4 are automatically driven by the motor 37 so that said bright line position becomes a predetermined position, thereby effecting automatic focus adjustment. According to the present invention, the amount into which the bright line is split is great and therefore, automatic focus adjustment can be accomplished more accurately than in the previously described embodiments.

What we claim is:

1. An eye-fundus examining instrument comprising:
   an optical system for examining the fundus of an eye, said optical system having movable means movable for focusing;
   an illumination system for illuminating the fundus of the eye;
   a mark projecting system for projecting a focus mark upon the fundus of the eye that can be focused on the fundus of the eye;
   a light-receiving system provided with a photosensor array for detecting the position of the focus mark image reflected by the fundus of the eye, the detected position of the focus mark image indicating the condition of focus of the focus mark on the fundus of the eye;
   observation means, coupled to said optical system, for observing therethrough the image of the fundus of the eye and the focus mark image;
   focusing means for simultaneously focusing said optical system, said mark projecting system and said light-receiving system relative to the fundus of the eye;
   manual control means for manually controlling said focusing means;
   drive means for driving said focusing means; and
   a circuit electrically coupled to said photosensor array for controlling said drive means.

2. An instrument according to claim 1, further comprising a second projecting system for projecting a reference mark upon the fundus of the eye and capable of being operated simultaneously and in conjunction with said mark projecting system.

3. An instrument according to claim 2, wherein said reference mark can be selectively rendered inoperative.

4. An instrument according to claim 1, further comprising a third projecting system for projecting a reference mark upon said observation means.

5. An instrument according to claim 1, further comprising position detecting means for detecting the amount of movement of said movable means and applying the detected information to said circuit.

6. An instrument according to claim 1, wherein said light-receiving system has a positive cylindrical lens adjacent to said photosensor array.

7. An instrument according to claim 1, wherein said observation means has a video camera and display means coupled to said video camera.

8. An eye-fundus camera comprising:
an eye examining apparatus, for examining an eye, provided with photosensitive means, fixed optical means for forming the image of the fundus of the eye on said photosensitive means, movable means movable for focusing, a shutter disposed on that side of the photosensitive means which is adjacent to said fixed optical means, a finder for observing therethrough the fundus of the eye, and an illumination system for illuminating the fundus of the eye;
a mark projecting system for projecting a focus mark upon the fundus of the eye that can be focused on the fundus of the eye;
a light-receiving system provided with a photosensor array for detecting the position of the focus mark image reflected by the fundus of the eye, the detected position of the focus mark image indicating the condition of focus of the focus mark on the fundus of the eye;
drive means for moving said movable means and at the same time, effecting the focusing of said mark projecting system and said light-receiving system; and
a control circuit coupled to said photosensor array for controlling said drive means to cause said focus mark image to rest at a reference position on said photosensor array.

9. A camera according to claim 8, wherein said control circuit has a reference position setting circuit for providing a reference signal corresponding to the time when the focus mark image has been formed at the reference position, a position detecting circuit for making a position signal fron the output of said photosensor array, and a comparator circuit for comparing said position signal with said reference signal and generating a signal for driving said drive means until the difference between said two signals becomes zero.

10. A camera according to claim 9, wherein said position detecting circuit determines, as the position of the focus mark, the peak position of a mountain-like signal appearing at the read-out starting time point of said photosensor array or first from a time point in a predetermined time delay after said read-out starting time point, among several mountain-like signals in which the differentiated value of the output of said photosensor array appears beyond the level value of a level setting circuit.

11. A camera according to claim 8, wherein said control circuit has a malfunctioning prevention circuit which generates a signal for stopping said drive means when a quantity of light exceeding a predetermined level is incident on said photosensor array.

12. A camera according to claim 11, wherein said malfunctioning prevention circuit displays by display means when a quantity of light exceeding a predetermined level is incident on said photosensor array.

13. A camera according to claim 8, wherein said control circuit has a non-stop preventing a circuit which generates a signal for stopping said drive means when said photosensor array does not receive the focus mark image even if the movable means of said eye examining apparatus is reciprocally moved over a predetermined number of times.

14. A camera according to claim 13, wherein said non-stop preventing circuit also generates a warning display signal when it generates the signal for stopping said drive means.

15. A camera according to claim 8, wherein said control circuit has a speed control circuit which generates a signal for driving said drive means at a high speed when the focus mark image formed on said photosensor array is spaced apart from said reference position by greater than a predetermined distance.

16. A camera according to claim 8, wherein said control circuit has a reset circuit which generates a signal for driving said drive means so that the focus of said eye examining apparatus is coincident with the division of zero diopter when one cycle of photographing has been terminated.

17. A camera according to claim 8, wherein said control circuit has a gain control circuit for varying the gain of said control circuit in a staircase-like fashion in accordance with the peak value in the pre-scanning of said photosensor array and the gain in said scanning.

18. A camera according to claim 8, further comprising a second projecting system for projecting a reference mark upon the fundus of the eye and cooperable with said mark projecting system, said second projecting system stopping projection of the reference mark when the focus mark image formed on said photosensor array is spaced apart from said reference position by greater than a predetermined distance.

19. A camera according to claim 18, wherein said focus mark and said reference mark are in a linear form.

20. A camera according to claim 19, wherein the wavelengths of the light beams forming said focus mark and said reference mark are included in the infrared wavelength range.

* * * * *

UNITED STATES PATENT AND TRADEMARK OFFICE
CERTIFICATE OF CORRECTION

PATENT NO. : 4,412,728

DATED : November 1, 1983

INVENTOR(S) : TOSHIO SAKANE, ET AL.

It is certified that error appears in the above-identified patent and that said Letters Patent is hereby corrected as shown below:

Column 4

Line 62, change "an" to --and--.

Column 8

Line 34, between "signals" and "99", insert --on lines--.

Column 9

Line 33, between "is", first occurrence, and "A", delete "a",

Line 37, change "Q", first occurrence, to --$\bar{Q}$--,

Line 38, change "Q" to --$\bar{Q}$--,

Line 46, change "Q", second occurrence, to --$\bar{Q}$--,

Line 56, change "Q" to --$\bar{Q}$--

Line 62, change "Q" to --$\bar{Q}$--.

Column 10

Line 2, change "As" to --At--,

UNITED STATES PATENT AND TRADEMARK OFFICE
CERTIFICATE OF CORRECTION

PATENT NO. : 4,412,728   Page 2 of 3

DATED : November 1, 1983

INVENTOR(S) : TOSHIO SAKANE, ET AL.

It is certified that error appears in the above-identified patent and that said Letters Patent is hereby corrected as shown below:

Column 10

Line 7, change "liner", both occurrence, to --liners--,

Line 13, change "Q" to --$\overline{Q}$--,

Line 48, between "number" and "of", insert --)--,

Line 54, change "an" to --the--.

Column 11

Line 7, change "time" to --timing--,

Line 56, after "resets", delete --.--.

Column 12

Line 2, change "comparatos" to --comparators--.

Column 13

Line 23, between "only" and "the", insert --when--,

Line 59, change "cylinder" to --cylindrical--,

Column 18, line 3
Claim 10 (next to last line)

Change "of" to --by--.

UNITED STATES PATENT AND TRADEMARK OFFICE
CERTIFICATE OF CORRECTION

PATENT NO. : 4,412,728

DATED : November 1, 1983

INVENTOR(S) : TOSHIO SAKANE, ET AL.

It is certified that error appears in the above-identified patent and that said Letters Patent is hereby corrected as shown below:

Column 18, line 15
Claim 13, line 2

Delete "a", second occurrence.

Signed and Sealed this

Tenth Day of April 1984

[SEAL]

Attest:

GERALD J. MOSSINGHOFF

Attesting Officer

Commissioner of Patents and Trademarks